United States Patent [19]
Shlenker et al.

[11] Patent Number: 5,549,924
[45] Date of Patent: Aug. 27, 1996

[54] METHOD OF FORMING A MEMBRANE, ESPECIALLY A LATEX OR POLYMER MEMBRANE, INCLUDING A DEACTIVATING BARRIER AND INDICATING LAYER

[75] Inventors: Robin R. T. Shlenker, Denver; David J. Lester, Littleton; Clive C. Solomons, Denver, all of Colo.

[73] Assignee: Robin Renee Thill Shlenker, Malibu, Calif.

[21] Appl. No.: 291,002

[22] Filed: Aug. 15, 1994

Related U.S. Application Data

[63] Continuation-in-part of Ser. No. 976,881, Nov. 16, 1992, Pat. No. 5,338,565, which is a continuation of Ser. No. 825,546, Jan. 24, 1992, Pat. No. 5,165,953, which is a continuation-in-part of Ser. No. 536,772, Jun. 12, 1990, Pat. No. 5,130,159, and a continuation-in-part of Ser. No. 536,773, Jun. 12, 1990, Pat. No. 5,128,168, said Ser. No. 536,772, and Ser. No. 536,773, each is a continuation-in-part of Ser. No.482,978, Feb. 22, 1990, Pat. No. 5,045,341, which is a continuation-in-part of Ser. No. 246,337, Sep. 19, 1988, Pat. No. 4,935,260, which is a continuation-in-part of Ser. No. 143,184, Jan. 13, 1988, Pat. No. 4,919,966, which is a continuation-in-part of Ser. No. 074,629, Jul. 17, 1987, Pat. No. 4,771,482.

[51] Int. Cl.$^6$ .............................. A01N 1/02; A41D 19/00; A61F 6/04

[52] U.S. Cl. .................. 427/2.3; 2/168; 128/844; 424/404; 427/407.1

[58] Field of Search ............... 2/167, 168; 128/844; 424/404; 427/2.25, 2.26, 2.28, 2.3, 2.31, 407.1; 604/46, 332; 606/236

[56] References Cited

U.S. PATENT DOCUMENTS

| | | | |
|---|---|---|---|
| D. 300,463 | 3/1989 | Nemec et al. | D24/17 |
| 1,954,262 | 4/1934 | Potter | 2/159 |

(List continued on next page.)

FOREIGN PATENT DOCUMENTS

| | | |
|---|---|---|
| 624862 | 8/1989 | Australia . |
| 620913 | 9/1989 | Australia . |
| 654162 | 12/1991 | Australia . |
| 2058210 | 2/1995 | Canada . |
| 0141628 | 10/1984 | European Pat. Off. . |
| 0147970 | 12/1984 | European Pat. Off. . |
| 0229862 | 1/1986 | European Pat. Off. . |
| 0287204 | 2/1988 | European Pat. Off. . |
| 0299802 | 7/1988 | European Pat. Off. . |
| 0306389 | 8/1988 | European Pat. Off. . |
| 328421A2 | 8/1989 | European Pat. Off. . |
| 0368456 | 9/1989 | European Pat. Off. . |
| 0427997 | 10/1990 | European Pat. Off. . |
| 0443870 | 2/1991 | European Pat. Off. . |
| 2623087 | 3/1987 | France . |
| 0442551 | 4/1927 | Germany . |
| 1917699 | 4/1969 | Germany . |

(List continued on next page.)

Primary Examiner—Michael Lusignan

[57] ABSTRACT

Single and multiple layer membranes such as gloves and condoms include one or more deactivating barrier layers and/or indicating layers to indicate to a user membrane breach or the presence of a harmful substance in blood or body fluids. A membrane may include one or more permeable or semipermeable layers to disperse contained substances such as lubricants, biocides, spermicides, or indicators outwardly, and may also include permeable or semipermeable layers to allow transmission of body fluids or other environmental fluids inwardly into contact with an indicating or treating substance. An intermediate layer of a multi-layer membrane may include a substance to wipe, cleanse, sterilize, or otherwise treat a piercing needle. A membrane may include a sealing or coating to entrap indicators or other agents such as biocides therein. A method of making membranes such as gloves results in a double glove having discrete inner or outer layers joined only in a cuff region. Admixing of gentian violet with latex prior to membrane formation provides biocidal properties, anti-aging effects prolonging shelf-life and tear resistance, and reduces allergic reactions in latex-allergic users.

37 Claims, 2 Drawing Sheets

U.S. PATENT DOCUMENTS

| | | | |
|---|---|---|---|
| 2,410,460 | 11/1946 | Robinson | 128/294 |
| 2,586,674 | 2/1952 | Lonne | 128/294 |
| 2,792,835 | 5/1957 | Ferguson | 128/260 |
| 3,079,351 | 2/1963 | Staneslow et al. | 260/3 |
| 3,110,035 | 11/1963 | LaHue | 2/168 |
| 3,121,877 | 2/1964 | Ginter | 2/159 |
| 3,342,182 | 9/1967 | Charos | 128/260 |
| 3,384,083 | 5/1968 | Cozza et al. | 128/260 |
| 3,390,214 | 6/1968 | Woods | 264/45 |
| 3,496,938 | 2/1970 | Furuse et al. | 128/271 |
| 3,633,216 | 1/1972 | Schonholtz | 2/168 |
| 3,672,351 | 6/1972 | Ubersax | 128/26 |
| 3,710,795 | 1/1973 | Higuchi et al. | 128/260 |
| 3,911,501 | 10/1975 | Seltzer | 2/167 |
| 3,971,499 | 7/1976 | Goodrich, Jr. et al. | 228/54 |
| 3,975,775 | 8/1976 | Alsop | 2/163 |
| 4,062,834 | 12/1977 | Gilding et al. | 260/77.5 AA |
| 4,112,138 | 9/1978 | Davis et al. | 427/150 X |
| 4,143,423 | 3/1979 | Sternlieb | 2/168 |
| 4,185,330 | 1/1980 | Stager | 2/164 |
| 4,214,321 | 7/1980 | Nuwayser | 2/167 |
| 4,286,592 | 9/1981 | Chandrasekaran | 128/260 |
| 4,286,593 | 9/1981 | Place et al. | 128/260 |
| 4,302,852 | 12/1981 | Joung | 2/167 |
| 4,332,243 | 5/1982 | Gutnick | 128/132 R |
| 4,377,567 | 3/1983 | Geho | 252/316 X |
| 4,404,197 | 9/1983 | Fox, Jr. et al. | 424/229 |
| 4,415,548 | 11/1983 | Reddy | 264/129 X |
| 4,427,003 | 1/1984 | Fennimore et al. | 427/341 X |
| 4,432,357 | 2/1984 | Pomeranz | 604/327 X |
| 4,438,177 | 3/1984 | Potter et al. | 428/355 |
| 4,446,124 | 5/1984 | Fox, Jr. et al. | 8/94.11 X |
| 4,446,860 | 5/1984 | Gutnick | 604/328 X |
| 4,471,538 | 9/1984 | Pomeranz et al. | 2/159 X |
| 4,499,154 | 2/1985 | James et al. | 428/494 |
| 4,512,337 | 4/1985 | Leveskis | 128/113 |
| 4,522,819 | 6/1985 | Fox, Jr. et al. | 514/187 |
| 4,534,078 | 8/1985 | Viesturs et al. | 5/452 |
| 4,535,078 | 8/1985 | Fox, Jr. et al. | 514/157 |
| 4,545,841 | 10/1985 | Jackrel | 156/290 |
| 4,559,223 | 12/1985 | Fox, Jr. | 514/157 X |
| 4,563,485 | 1/1986 | Fox, Jr. et al. | 523/113 |
| 4,581,028 | 4/1986 | Fox, Jr. et al. | 623/2 |
| 4,592,920 | 6/1986 | Murtfeldt | 427/387 X |
| 4,595,001 | 6/1986 | Potter et al. | 128/156 |
| 4,655,202 | 4/1987 | Potter et al. | 524/413 X |
| 4,657,006 | 4/1987 | Rawlings et al. | 604/307 X |
| 4,662,006 | 5/1987 | Ross, Jr. | 2/158 |
| 4,672,956 | 6/1987 | Potter et al. | 427/389.9 X |
| 4,675,347 | 6/1987 | Mochizuki et al. | 523/122 |
| 4,704,130 | 11/1987 | Gilding et al. | 623/66 |
| 4,747,401 | 5/1988 | Potter et al. | 604/369 X |
| 4,771,482 | 9/1988 | Shlenker | 2/161 R |
| 4,798,201 | 1/1989 | Rawlings et al. | 428/199 X |
| 4,813,966 | 3/1989 | Gilding et al. | 623/66 |
| 4,851,266 | 7/1989 | Momose et al. | 427/353 |
| 4,853,978 | 8/1989 | Stockum | 2/167 |
| 4,867,968 | 9/1989 | Allen | 523/121 X |
| 4,876,293 | 10/1989 | Durney et al. | 523/122 |
| 4,881,277 | 11/1989 | Hogle | 2/169 |
| 4,888,007 | 12/1989 | Loeb et al. | 604/352 |
| 4,901,372 | 2/1990 | Pierce | 2/167 |
| 4,919,966 | 4/1990 | Shlenker | 2/159 X |
| 4,930,522 | 6/1990 | Busnel et al. | 128/844 |
| 4,935,260 | 6/1990 | Shlenker | 2/159 X |
| 4,935,308 | 6/1990 | Guerra et al. | 428/518 |
| 4,977,903 | 12/1990 | Haines | 128/842 |
| 5,008,110 | 4/1991 | Benecke et al. | 424/448 |
| 5,010,883 | 4/1991 | Rawlings et al. | 428/220 X |
| 5,019,096 | 5/1991 | Fox, Jr. et al. | 623/1 |
| 5,024,852 | 6/1991 | Busnel et al. | 2/168 X |
| 5,031,245 | 7/1991 | Milner | 2/168 |
| 5,045,341 | 9/1991 | Shlenker | 2/167 X |
| 5,071,656 | 12/1991 | Lee et al. | 424/448 |
| 5,073,365 | 12/1991 | Katz et al. | 424/489 |
| 5,080,646 | 1/1992 | Theeuwes et al. | 604/20 |
| 5,084,514 | 1/1992 | Szczechura et al. | 525/123 |
| 5,087,240 | 2/1992 | Sibalis | 604/20 |
| 5,089,205 | 2/1992 | Huang et al. | 264/255 |
| 5,108,710 | 4/1992 | Little et al. | 422/104 |
| 5,115,805 | 5/1992 | Bommannan et al. | 604/20 X |
| 5,122,116 | 6/1992 | Kriesel et al. | 604/89 |
| 5,128,168 | 7/1992 | Shlenker et al. | 2/167 X |
| 5,130,159 | 7/1992 | Shlenker et al. | 2/167 X |
| 5,141,748 | 8/1992 | Rizzo | 424/425 |
| 5,141,750 | 8/1992 | Lee et al. | 424/448 |
| 5,147,296 | 9/1992 | Theeuwes et al. | 604/20 |
| 5,156,949 | 10/1992 | Luciw et al. | 435/5 |
| 5,160,316 | 11/1992 | Henley | 604/20 |
| 5,163,899 | 11/1992 | Sibalis | 604/20 |
| 5,164,189 | 11/1992 | Farhadich et al. | 424/448 |
| 5,165,953 | 11/1992 | Shlenker et al. | 2/167 X |
| 5,169,382 | 12/1992 | Theeuwes et al. | 604/20 |
| 5,169,383 | 12/1992 | Gyory et al. | 604/20 |
| 5,175,003 | 12/1992 | Goldman | 424/484 |
| 5,223,262 | 6/1993 | Kim et al. | 424/448 |
| 5,224,373 | 7/1993 | Williams et al. | 73/29.02 |
| 5,230,896 | 7/1993 | Yeh et al. | 824/443 |
| 5,231,975 | 8/1993 | Bommannan et al. | 604/204 |
| 5,232,438 | 8/1993 | Theeuwes et al. | 604/20 |
| 5,234,690 | 8/1993 | Chiang et al. | 424/448 |
| 5,234,957 | 8/1993 | Mantelle | 514/722.6 |
| 5,250,028 | 10/1993 | Theeuwes et al. | 604/85 |
| 5,260,069 | 11/1993 | Chen | 424/451 |
| 5,262,165 | 11/1993 | Govil et al. | 424/448 |
| 5,266,325 | 11/1993 | Kuzma et al. | 424/422 |
| 5,267,957 | 12/1993 | Kriesel et al. | 604/85 |
| 5,273,755 | 12/1993 | Venktrama et al. | 424/448 |
| 5,273,756 | 12/1993 | Fallon et al. | 424/448 |
| 5,273,757 | 12/1993 | Jaeger et al. | 424/448 |
| 5,284,660 | 2/1994 | Lee et al. | 424/449 |
| 5,290,561 | 3/1994 | Farhadieh et al. | 424/449 |
| 5,292,515 | 3/1994 | Moro et al. | 424/422 |
| 5,293,948 | 3/1994 | Finley | 2/243.1 |
| 5,306,250 | 4/1994 | March et al. | 604/104 |
| 5,335,373 | 8/1994 | Dangman et al. | 2/167 X |
| 5,338,565 | 8/1994 | Shlenker et al. | 427/2.25 |
| 5,357,636 | 10/1994 | Dresdner, Jr. et al. | 2/167 X |

FOREIGN PATENT DOCUMENTS

| | | |
|---|---|---|
| 3411957 | 3/1984 | Germany. |
| 540241 | 4/1942 | United Kingdom. |
| 2104087A | 3/1983 | United Kingdom. |
| 8501208 | 3/1985 | WIPO. |
| 8904647 | 6/1989 | WIPO. |
| 9001956 | 3/1990 | WIPO. |

METHOD OF FORMING A MEMBRANE, ESPECIALLY A LATEX OR POLYMER MEMBRANE, INCLUDING A DEACTIVATING BARRIER AND INDICATING LAYER

CROSS-REFERENCE TO RELATED APPLICATIONS

This application is a continuation-in-part of U.S. patent application Ser. No. 07/976,881, filed Nov. 16, 1992, now U.S. Pat. No. 5,338,565, which is a continuation of U.S. patent application Ser. No. 07/825,546, filed Jan. 24, 1992, now U.S. Pat. No. 5,165,953, which is a continuation-in-part of both U.S. patent application Ser. No. 07/536,772 filed Jun. 12, 1990, now U.S. Pat. No. 5,130,159 and U.S. patent application Ser. No. 07/536,773 filed Jun. 12, 1990, now U.S. Pat. No. 5,128,168, both of which are continuations-in-part of U.S. patent application Ser. No. 07/482,978, filed Feb. 22, 1990, now U.S. Pat. No. 5,045,341, which is a continuation-in-part of U.S. patent application Ser. No. 07/246,337, filed Sep. 19, 1988, now U.S. Pat. No. 4,935,260, which is a continuation-in-part of U.S. patent application Ser. No. 07/143,184, filed Jan. 13, 1988, now U.S. Pat. No. 4,919,966, which is a continuation-in-part of U.S. patent application Ser. No. 07/074,629, filed Jul. 17, 1987, now U.S. Pat. No. 4,771,482. All of these applications and patents are owned by the same Applicant. The entire disclosures of each of the foregoing patent applications and patents are hereby incorporated by reference herein.

BACKGROUND OF THE INVENTION

The present invention relates to membranes formed from materials including latex, polyurethane, polyethylene, rubber, and other polymers and elastomers. Known applications of such membranes include surgical and examination gloves, condoms, diaphragms, dressings, sheaths, slippers, overshoes, sterile bands, catheters, tubing, drapes, gut openings, mouth pieces, baby nipples, intra gastric nasal tubes, nasal gastric tubes, kidney shunts, eye and brain shunts, dental dams, dental braces, sub-clavian vein and artery shunts, and colostomy bags. Typically, such membranes in use contact a person's or animal's skin or other tissues.

In recent years, there has been a growing interest in improving such membranes to provide increased protection against the transmission of viruses such as hepatitis and HIV, as well as other pathogens and harmful agents.

SUMMARY OF THE INVENTION

The present invention discloses several embodiments which provide membranes with an improved resistance to transmission of viruses and other harmful agents, and capabilities to disinfect needles and other membrane piercing objects, and also discloses the provision of one or more indicating layers to detect and indicate membrane breach and the presence of viruses, and other pathogens, as well as harmful chemicals.

In one aspect of the invention, a membrane of multi-layer construction includes one or more inner-layers, which serve as reservoirs for substances or agents such as biocides, lubricants, or indicators, which can pass through one or more permeable or semi-permeable outer layers to make the reservoir substance available on the outside of the membrane, or to alternatively prevent exterior transmission of reservoir substances while allowing exterior substances to pass at least partially through the membrane. As an alternative to permeability, substantially impermeable layers may transmit the substance or agent upon rupture or piercing and completely contain the substances at all other times.

According to another aspect of the invention, a membrane of multi-layer construction includes one or more inner-layers, which serve as reservoirs for substances or agents such as biocides, lubricants, or indicators, which can contact or otherwise interface with substances passing through one or more outer layers of the membrane and which may react with, indicate the presence of, or otherwise respond to the presence of the substance originally outside the membrane. Such multi-layer membranes can be used to provide anti-microbial, disinfectant, or other killing or disabling action to infectious agents, microbes, viruses, or bacteria, through selective or controlled flow of the inner substances or agents to the surface of the membrane.

According to another aspect of the invention, a multi-layer membrane provides a site for indicating materials such as a DNA probe based reaction such as Chiron's n"Branched DNA Probe", Hoffman-LaRoche's "Polymerase Chain Reaction" technique, or conventional color change indicator reactions, titration reactions, reactions to detect Ph, and reactions to detect chemicals, viruses or other pathogens. The multi-layer membrane includes one or more permeable or semi-permeable layers to allow migration of a material to be detected through one or more outer layers and into contact with an indicating material or system. One of the layers may be impermeable to prevent migration beyond the indicators or other reservoir materials.

In another aspect of the invention, indicators to detect chemicals, viruses, or other pathogens are admixed with the material of the membrane, or with a layer of a multi-layer membrane, or coated on an outer layer of the membrane or multi-layer membrane.

Another aspect of the invention involves the provision of an indicator to indicate a breach of a membrane. Indication may be provided by color change, shade change, e.g., darker or lighter, temperature change, or tactile change, e.g., stiffness or tightness. Indicators such as cobalt chloride can indicate membrane breach by reacting in the presence of moisture.

In another aspect of the invention, a permeable or semi-permeable membrane of multi-layer construction includes one or more inner-layers which serve as reservoirs for substances or agents such as biocides, lubricants, hydrogels, or indicators. The substances or agents can pass through the outer layer or layers to make the reservoir substance available on the outside of the membrane.

In another aspect of the invention, one or more semi-permeable or permeable membrane layers permit migration of a substance in a predetermined direction. For example, viruses or other pathogens may migrate inwardly into contact with an indicator or biocide. Additionally or alternatively, biocides, lubricants, spermicides, antiseptics, or indicators, may migrate outwardly.

In another aspect of the invention, a single or multi-layer membrane includes an indicator located on an inner or outer surface to detect the presence of a virus or other harmful material disposed exteriorly of the membrane and/or also indicate transmission of a harmful material either partially or entirely through the membrane.

Another aspect of the invention includes the provision of a tactile-feeling enhancing liquid or gel between layers of a multi-layer membrane.

Another aspect of the invention involves the dispersion of micro-fibers or fibers such as Kevlar within or onto a membrane forming substance prior to or during membrane formation to increase membrane strength and penetration resistance.

In one aspect of the invention, the membrane includes an indicator which provides a prompt identifiable reaction in the presence of a harmful substance to alert a user. Example indicators include a DNA probe such as those developed by Chiron or Hoffman-LaRoche to detect the presence of particular viruses, or conventional color change indicator technology such as phenylthaline reactions or Ph indicator materials, 10 chromophores, or dyes which change in the presence of the substance to be detected.

In one aspect of the invention, a single or multi-layer membrane effects transport across one or more membrane layers by capillary or wicking action. The membrane or one or more layers may also constitute a size selective membrane to limit the size of viruses or microbes passing through. Additionally or alternatively, one or more of the membrane layers may be chemically selective. For example, membranes of the type used in filtration and purification procedures may be employed.

In another aspect of the invention, a membrane including a permeable or semi-permeable outer or inner layer includes a sealing treatment or coating to entrap indicators or biocide agents therein.

The invention also contemplates the provision of an indicator dispersed throughout a membrane or restricted to a certain spot or area on or in the membrane, such as in or on dots or stripes. The indicator may be added to the membrane during formation or after completion.

In another aspect of the invention, a needle treatment substance in one or more inner layers of a membrane functions to clean, coat, wipe, scrape, cleanse, disinfect, render less harmful, or otherwise treat a needle or other membrane piercing object.

Another aspect of the invention discloses a method of making a multi-layered membrane, such as a glove or condom, in which the layers are joined only in a cuff or top region.

In another aspect of the invention, a method of admixing gentian violet with wet latex prior to membrane formation increases membrane strength and reduces or eliminates allergic affects in latex-allergic individuals.

In another aspect of the invention an adhesive backed patch includes an antiseptic or cleansing agent which contacts a needle or catheter piercing therethrough.

DESCRIPTION OF THE PREFERRED EMBODIMENTS

Needle Treating Layer

Figure 1:
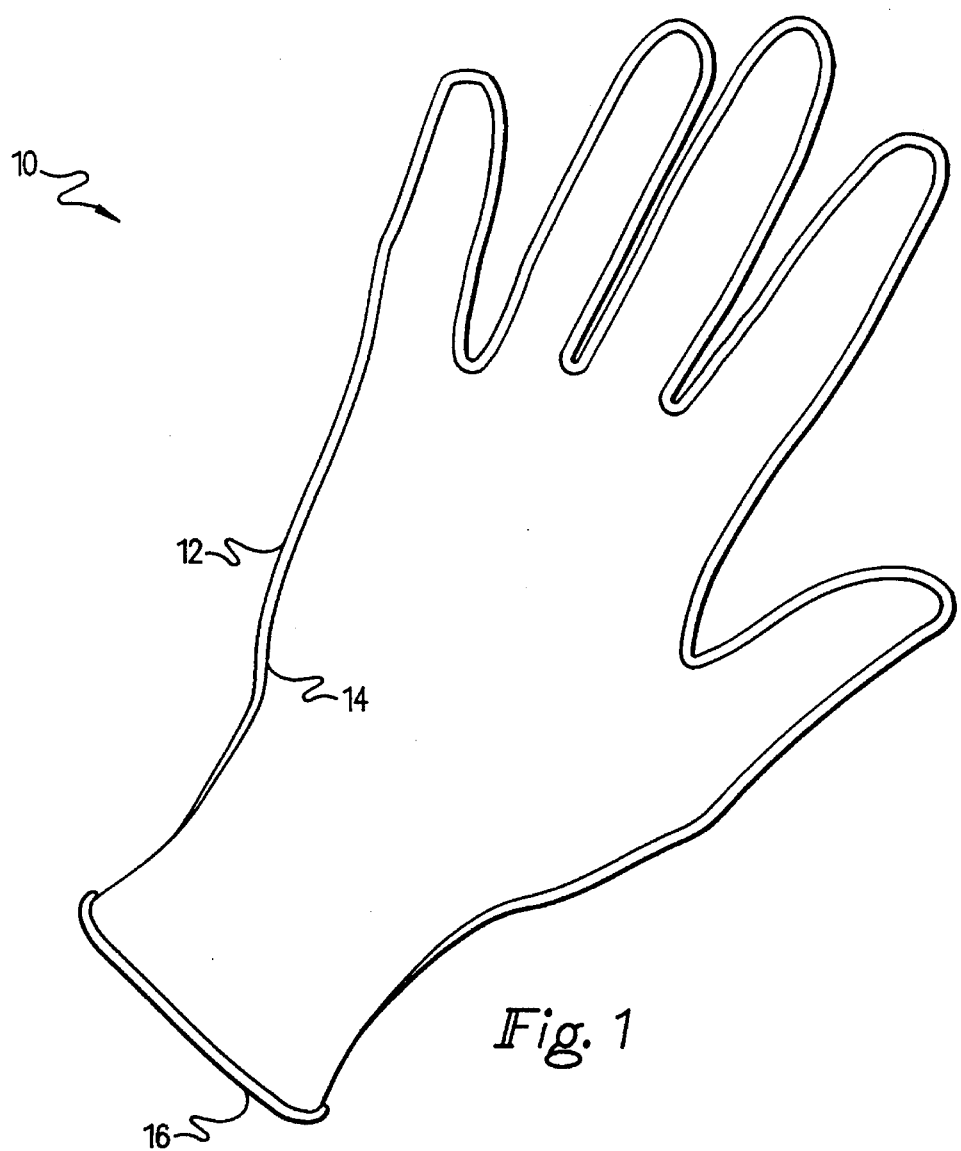
FIG. 1 depicts a diagrammatic plan view illustrating a double glove produced according to a method of the present invention.

Needles, both hollow core and solid, as well as other sharp objects such as catheters, scalpels, wires, or bone fragments, have long been a concern for health care professionals and others in regard to the infection which they can transmit. Needles are usually in sterile condition when removed from their wrappers, however they can be inadvertently contaminated when they pass through a person's body and are potentially contaminated when they are removed from an infected patient's body.

It is common for health care workers and hospital staff to be accidentally stuck by needles or other sharp objects both during and after their use.

Pursuant to the present invention, a material is incorporated within a multi-layer membrane, such as a glove, to clean, coat, wipe, scrape, cleanse, disinfect, render less harmful or otherwise treat a needle or other sharp object passing therethrough.

A membrane formed from liquid latex, solvent cast membranes, liquid polymers, or elastomers may be formed by dip forming, the use of fluidized beds, or spraying the liquid material onto a former. After deposit of one or more layers, a middle layer including a material having treatment properties is deposited. Thereafter, one or more outer layers are formed and the membrane is cured or set according to conventional techniques.

Suitable polymers for use in producing membranes pursuant to the invention include prepolymers, i.e. low molecular weight polymers and polymer precursors, prepolymers and polymer precursors dissolved in solvents, liquid monomers, and liquid monomers dissolved in solvents. Specific examples include low molecular weight polymers such as silicone rubber (polydimethyl siloxane: $HO\text{-}(Si\text{-}(CH_3)_2\text{-}O\text{-})_n\text{-}H$) with n from 2 to 200; polymer precursors such as low molecular weigh diol, e.g. $HO\text{-}((CH_2)_4\text{-}O)_{18})\text{-}H$ and low molecular weight diisocyanate, e.g. $OCN\text{-}C_6H_6\text{-}CH_2\text{-}C_6H_6\text{-}NCO$ which when mixed and polymerized form polyurethane. Example solvents for low molecular weight polymers include xylene and n-hexane. Suitable solvents for polymer precursors include dimethyl formamide and dimethyl sulfoxide. Example liquid monomers include alpha-alkyl cyanoacrylate, where the alkyl group can be -methyl, -ethyl, -propyl, etc. Example solvents for liquid monomers include dimethyl formamide. In the context of this description, the terms prepolymer, polymer, and polymer precursors include mixtures of one or more prepolymers, polymers, or polymer precursors.

In one embodiment of the invention, the needle or sharp object treating layer comprises a gummy coating such as urethane of a gum-like consistency, semi-cured latex, a gel, polymers, an adhesive, or a pituitous substance, with or without an admixed biocide, antiseptic, or sterilizing agent, as an inner layer.

As the needle or other object pierces the membrane, the treatment substance tends to stick to it, coat it, cleanse it, or otherwise deactivate any harmful substances which might adhere thereto. The mechanics of the needle or sharp object treatment mechanism may include both chemical and mechanical aspects. For example, the layer preferably includes a biocide or antiseptic effective against pathogens. Additionally, the layer may also function to wipe blood and other bodily fluids from the needle as it passes therethrough.

Alternately, abrasive materials of a fine texture capable of physically dislodging or scraping materials coated on the needle may be used individually or in combination.

Example treatment chemicals added to a biocide in the inner needle treatment layer include polyethylene oxide, and a mixture of polyethylene oxide and glycerin. In forming latex membranes, a first latex layer is deposited by dipping or spraying or by other conventional techniques. A biocide, such as a gentian violet solution, is thickened with a mixture of polyethylene oxide and glycerin. The thickened mixture is applied over the latex layer, allowed to dry to some extent, and then coated with one or more latex layers.

The needle treatment layer may also include adhesive or film-forming materials which would form a physical sheath or additional membrane over the needle or other sharp object and over other harmful agents thereon.

The needle treating layer or layers may also include a detergent or other agent which will modify the surface tension properties of harmful agents on the needle rendering it possible for a subsequent layer to physically remove, contain, disinfect, or render less harmful the harmful agent, or for it to be less prone to infect or contaminate the person or animal on the opposite side of the membrane.

The aforementioned approaches may be used individually or in combination and may be contained in the same layer or in separate layers of a multi-layer membrane. They may be coagulants or not and the use of natural latex and man-made latex or polymers or elastomer substitutes may be interchangeable.

Needle Treatment Patch

A needle treatment patch and a method for its use in assisting in disinfecting a needle or other sharp object after or during its use are described below.

In one embodiment a small adhesive backed patch or disc can be attached to the area which the needle is set to penetrate. The disc can be similar to a squashed or flattened vitamin E pellet which the needle pierces before piercing the skin. The disc includes an antimicrobial, antiseptic or cleansing ingredient which contacts the needle prior to piercing the skin and upon exiting the skin. The disc may be transparent to assist a health care professional in locating a vein or other target. Likewise, the adhesive may be disposed only around the outer periphery of the disc so that it would not be carried into the puncture.

The back side of the patch may include a biocide or antiseptic adapted to contact the skin of a patient or animal.

The disc may be constructed such that the weave or pattern allows penetration by the needle or syringe upon entering and then creates a wiping action upon being withdrawn back through the disc. The patch preferably includes an antimicrobial or disinfecting solution.

The biocide or antiseptic solution contained in both embodiments may be of a gel-like and/or sticky consistency to help coat the needle or seal it on the way out of the body or patch.

The patch may also be used in conjunction with insertion or attachment of catheters and ostomy products, and may be employed in conjunction with long term attachment of a catheter to inhibit growth and/or transmission of pathogens.

Suitable patch adhesives, as set forth in U.S. Pat. No. 5,234,957, the entire disclosure of which is incorporated by reference herein, include partially esterified polyacrylic acid polymers, including but not limited to, polyacrylic acid polymers crosslinked with a polyalkenyl polyether such as those commercially available from B. F. Goodrich, Cincinnati, Ohio, under the trademarks Carbopol 934, 934P, 940 and 941. Other suitable adhesives include natural or synthetic polysaccharides such as cellulose derivatives such as methylcellulose, cellulose acetate, carboxymethylcellulose, hydroxyethylcellulose and the like. Other suitable adhesives are pectin, a mixture of sulfated sucrose and aluminum hydroxide, hydrophilic polysaccharide gums such as natural plant exudates, including karaya gum, ghatti gum, tragacanth gum, xanthan gum, jaraya gum and the like, as well as seed gums such as guar gum, locust bean gum, psillium seed gum and the like.

Suitable biocides for use in membranes according to the disclosure of the instant application include phenols, acridine dyes, gentian violet (crystal violet), chlorhexadine, Triclosan, Nonoxynol 9, Gluconate, dextran sulphate, benzalkonium, betadyne, mercurochrome, silver salts, and an extract of blue-green algae, in addition to a long list of other suitable biocides appended to this description immediately prior to the claims.

Indicators And Multi-Layer Membranes

In most surgical settings the physician or surgeon does not know if the patient has a communicable disease carried by blood borne pathogens. It would be beneficial, especially for those in the operating room and emergency room, to have an indicator on their glove that would alert them when they are in contact with the patient's blood or body fluid that there is the presence of a harmful, contagious or potentially fatal substance in that fluid or blood.

The present invention contemplates the provision of indicating mechanisms to multi-dipped or solvent formed membranes, including, but not limited to, gloves and condoms. The present invention discloses the provision of indicators to alert a user to membrane breach, as well as to alert a user of dangerous substances present in blood and other body fluids.

As disclosed in U.S. Pat. No. 4,935,260, fluid reservoirs within a membrane may include colored, fluorescent, or reactive substances which serve as an indicator if the membrane is breached, defective or disturbed. The present invention contemplates the provision of a visual indication to a user of membrane breach by color change or appearance or other physical means.

An indicating change to a material in an inner layer of a multi-layer membrane can be triggered by the presence of air, moisture, body fluids, harmful substances, change in electrical activity, surface tension, or partial pressure. The indicating system responds to an exposure of the indicating element to an outside substance or change in the physical integrity of the surrounding membrane. Ph change in the inner material because of exposure to substances outside the membrane can be an additional indicating mechanism.

Other suitable indicators for use in membranes according to the present invention include indicating materials such as a DNA probe based reaction such as Chiron's "Branched DNA Probe", Hoffman-LaRoche's "Polymerase Chain Reaction" technique, or conventional color change indicator reactions, to detect chemicals, viruses or other pathogens. A multi-layer membrane may include one or more permeable or semi-permeable layers to allow migration of a material to be detected through the outer layers and into contact with an indicating material or system. Other suitable viral indicators and indicating methods are disclosed in U.S. Pat. Nos. 4,879,211; 4,942,122; 5,039,604; 5,093,230; 5,108,891;

5,149,623; 5,156,949; 5,208,321; 5,235,039; 5,260,189; 5,268,265; the entire disclosure of each of which are hereby incorporated by reference herein.

A method of making a membrane including a color indicator for membrane breach is set forth below.

1. Using conventional dipping, spraying, or other sheet forming techniques an initial layer is formed using elastomer materials such as latex, solvent cast membranes, liquid polymers, or elastomers, or polymer films. A second layer is created by conventional techniques such as coating or dipping (with or without a coagulant) including an indicating material such as dyes, crystals, reactants, colored agents, or congealing substances.
2. The dyes or indicators are selected to provide a noticeable change in appearance, feel, (stiffness, clumpyness, consistency), or temperature, to indicate to the user that the membrane is compromised.
3. One or more additional elastomeric membrane layers are then formed to at least partially contain the indicating substance.

The present invention also contemplates the provision to a multi-layer membrane of an indicator to detect and indicate the presence of pathogens in blood or other bodily fluids.

Outer membrane layers selected to be either impermeable, permeable, or selectively permeable to a substance included in a reservoir created between membrane layers, or to the substances, microbes or pathogens whose presence is to be detected. Instead of, or in addition to, the inclusion of various substances in a reservoir formed between membrane layers, the substances may be applied to inner or outer surfaces of the membrane after formation.

Multi-layer gloves according to the present invention, in addition to or instead of indicators, may also include one or more reservoirs disposed between adjacent membrane layers and containing one or more substances such as biocides, spermicides, antiseptics, gels, hydrogels, pituitous substances, cleansing agents, surfactants, detergents, abrasives, coating agents, wiping agents, fibers, tactile enhancing objects, and sheet forming agents, such that said substance is substantially contained between the adjacent layers. One or more of the multiple membrane layers may be permeable or semi-permeable to allow directional migration of (1) reservoir substances exteriorly to the membrane, or (2) exterior substances at least partially through the membrane.

Figure 4:
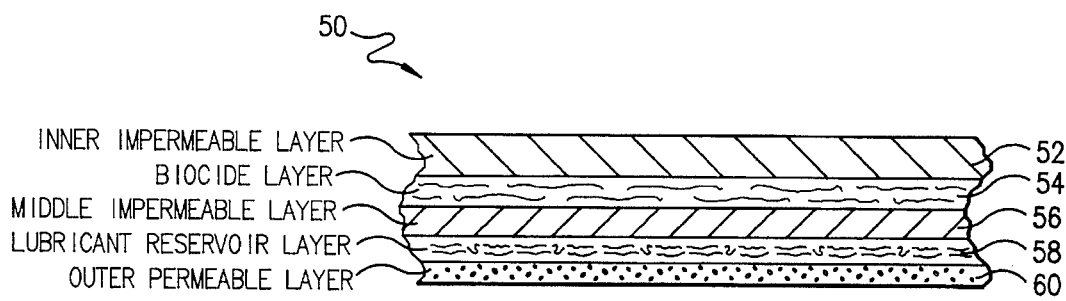
FIG. 4 is a cross-sectional view illustrating an example multi-layer membrane according to the present invention.

An example multi-layer membrane 50 according to the present invention is illustrated in FIG. 4. The membrane 50 may, for example, comprise a condom. An inner impermeable layer 52 may be formed from latex or from a polymer material. A biocide and/or spermicide such as Nonoxynol 9 at least partially fills a reservoir 54 formed between the inner layer 52 and a middle or intermediate impermeable layer 56, which may also comprise a latex or polymer material. A lubricant fills a reservoir 58 formed between the intermediate layer 56 and an outer permeable layer 60 to effect a controlled release of the lubricant through the pores of the permeable layer 60 over time. The permeable layer 60 may comprise a membrane with pores which open to permit the lubricant from reservoir 58 to pass through when stretched under pressure.

In the event of breach of the inner layer 52, seminal fluids will initially contact the biocide/spermicide in the reservoir 54, even in the event of a concurrent breach of the intermediate layer 56. Similarly, in the event of breach of the intermediate layer 56, vaginal fluids will also initially contact the biocide/spermicide in the reservoir 54, even in the event of a concurrent breach of the inner layer 52.

The methods of introducing or forming the inner layer or one or more intermediate or outer layers of multi-layer membranes pursuant to the present invention include dip forming methods and other techniques such as spray coating, fluidized bed deposition, vapor deposition, electrical discharge deposition, vacuum deposition, centrifugal coating, and extrusion.

Membranes or membrane layers pursuant to the invention may also include latex, elastomer, or polymer films where the membrane or membrane layer is coated with a desired substance such as biocides, indicators, spermicides, antiseptics, gels, hydrogels, pituitous substances, cleansing agents, surfactants, detergents, abrasives, coating agents, wiping agents, fibers, tactile enhancing objects, and sheet forming agents, and is then surface treated to contain the coated substance. Examples of such surface treatment methods include treatment with a chemical such as chlorine or bromine, coating with a sealant such as silicone or an acrylic, a heat treating process such as melting or glazing, treatment by exposure to reduced temperatures, mechanical treatment processes such as rolling, pressing, ultrasonics, or radio frequency heating. In each instance the common objective is the substantial containment of a desired substance on a surface of an inner, intermediate, or outer membrane layer.

The surface on one side may be designed to be impervious while the substance on the other side of the multi-layer membrane may be designed to be permeable or selectively permeable.

The indicator may be provided on an interior surface of single or multi-layer membranes, or on the outer surface, where it can be exposed to a pathogen or harmful substance or antibody of a harmful substance.

Figure 3:
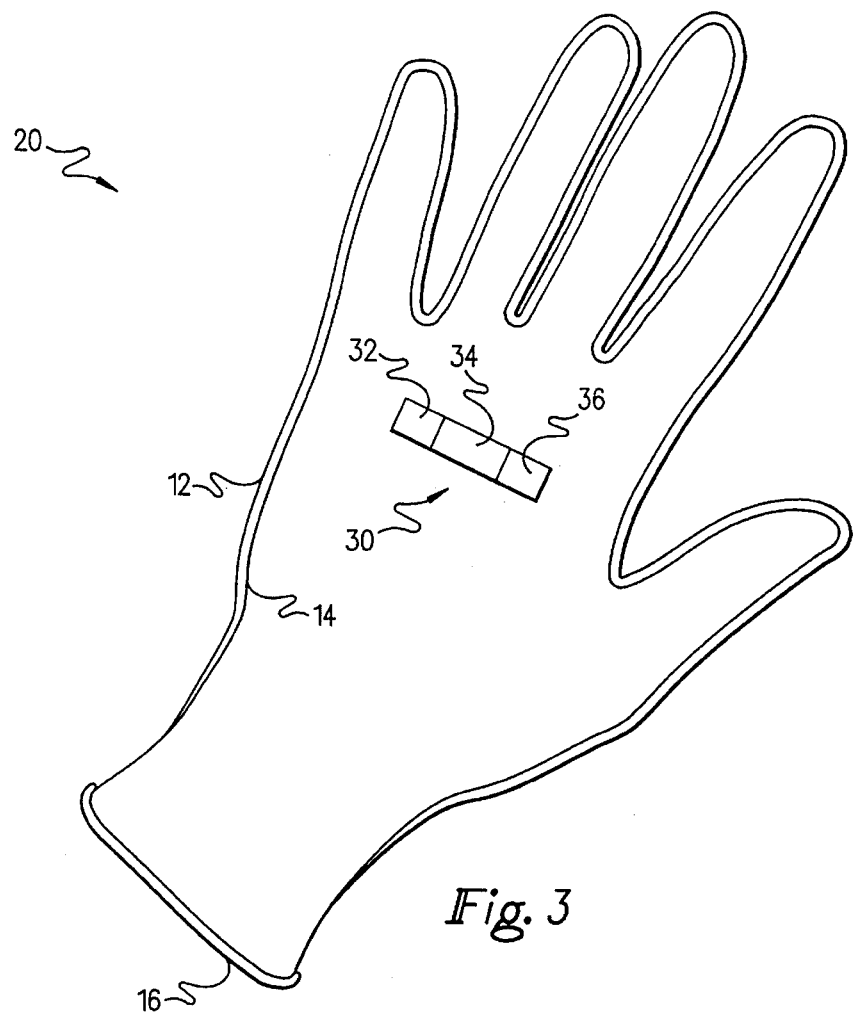
FIG. 3 is a diagrammatic plan view illustrating a double glove according to the present invention having an indicating strip with separate detecting regions to indicate the presence of different pathogens or other harmful agents or chemicals in the environment of the glove user.

FIG. 3 illustrates an example glove 20 according to the present invention which includes inner 14 and outer 12 layers joined at a cuff region 16. An indicating strip 30 bonded or otherwise attached to the outer surface of the glove 30 includes separate indicators in boxes or regions 32, 34, and 36 for detecting and indicating to the user the presence of pathogens or other harmful agents or chemicals in the user's environment. For example the indicator bar may show the presence of Strep in box 32, the presence of a retro-virus in box 34, and the presence of Staph in box 36.

The indicating substance may be more effectively retained by the membrane if the membrane comprises a film selected from the family of glow discharge treated polymers, such as polyethylene, tetrafluoroethylene PE (TFE/PE), polyethyleneterephthalate (PET), TFE/PET, polytetrafluoroethylene (PTFE), ehtylene glow discharge treated PET (E/PET) and hexamethyldisiloxane glow discharge treated PET (HMDS/PET).

The indicator preferably included in multi-layer membranes produces an identifiable reaction, alerting the wearer to the presence of a potentially harmful substance.

Indicators may be specific for any number of substances and microorganisms, including viruses (including HIV), bacteria, yeasts, undesirable and harmful chemicals, etc.

Specific viral indicators may include DNA Probe based reactions such as Chiron's "Branched DNA Probe", HoffmanLaRoche's "Polymerase Chain Reaction" technique, the elements of the P-24 antigen kit, the Abbot Lab preparation or mixed preparation for GP-120.

Additional examples of indicators include conventional color change indicator reactions where the material to be detected (pathogen, chemical, or other substance) could migrate through the outer membrane and reach the indicator system. Similarly, certain of these indicators could be admixed with the material of the membrane or a layer of the multi-layer membrane or coated on the outer layer of the membrane or multi-layer membrane.

For example, HIV and Hepatitis B belong to a family called the retro-virus family. Indicators that could pick up the presence of HIV in blood are the P-24 antigen kit, and the Abbot Lab preparation or mixed preparation for GP-120. In addition, other tests can pick up indications of the presence of a retro-virus or a lenti virus by reacting with a substance common to the virus family, like the envelope of the virus family. Indicators may also pick up anti-bodies to these harmful substances in bodily fluids such as blood, semen, or vaginal fluid. And it is particularly noted that one specific substance may be picked up instead of a family of harmful substances. Some of these indicators may be, but are not necessarily limited to, the family or group of synthetic peptides and epitopes.

Transdermal Trigger

When a glove is in use, a defect can sometimes be detected by various leak detector devices—some utilizing changes in the electrical properties or patterns of the material or material surface. These are of little benefit if the wearer is not in a position to change his gloves and remove the defective glove or pull another glove over it.

The present invention discloses a glove constructed in a multi-layered manner that contains a chemical that may be triggered to be released inside the glove, next to the hand to protect the wearer, until the time when he or she can take proper action.

The technology applied to the membrane is similar to existing transdermal patch technology. This technology is in use in nicotine patches and hormone releasing patches. They can provide a sustained release or a specific release upon a change in the electrical properties on the surface of, or a breach in integrity of, the membrane. Examples of transdermal patches are disclosed in U.S. Pat. Nos. 4,286,592; 4,627,429; 4,839,174; 4,921,475; 4,978,531; 5,008,110; 5,087,240; 5,163,899; 5,164,189; 5,230,896; 5,234,957; 5,262,165; 5,273,756; and 5,286,490; 5,290,561; the entire disclosures of each of which are hereby incorporated by reference herein.

The multi-layer glove preferably contains a reservoir of antiseptic/disinfectant which is released through the transdermal system upon deterioration of the glove film as indicated by a change in electrical properties, the presence of moisture or other indications of decrease in glove integrity.

Double Layer Membrane Dip Forming Method

In many applications, use of a double layer membrane can provide increased protection. For example, it is now an accepted practice for surgeons and other health care practitioners to don two pairs of gloves, one over the other to provide maximum protection from infection. Indeed, some studies show that the use of two gloves worn together reduces the occurrence of infection.

Such a double layer membrane configuration also creates a space which can serve as a reservoir, particularly when the layers of the membrane are joined at a cuff or top region. This reservoir can be used to contain a variety of materials including biocides, needle treating materials, tactile enhancing liquids or gels, lubricants, spermicides, hydrogels, and indicators.

Hydrogels may be of the type disclosed in U.S. Pat. No. 4,499,154, the entire disclosure of which is incorporated herein by reference. Hydrogels may function to absorb a biocide and to hold membrane layers apart, and can function as a coagulant or as a lubricant.

Examples of lubricants within the scope of this application include water soluble nontoxic chemical compounds that incorporate sodium or potassium in varying chemical combinations with carbonates, acetates, bicarbonates, acetate trihydrates and citrate dihydrate, as disclosed in U.S. Pat. No. 4,143,423, the entire disclosure of which is hereby incorporated by reference herein. Other suitable lubricants include microspheres as described in U.S. Pat. No. 5,073,365, the entire disclosure of which is hereby incorporated by reference herein.

It is possible to form a double glove or other double membrane in a multi-dip manufacturing process. Latex gloves and condoms are conventionally produced using a dip forming method in which shaped formers are dipped into vats of liquid latex. A method of making a double layer latex membrane pursuant to the present invention includes the following steps:

1. Clean formers.
2. Heat formers for eight minutes at 210°–220° F. degrees.
3. Dip into coagulating solution such as $CaCO_3$ plus alcohol plus $NO_3$, (or Calcium Carbonate plus alcohol plus nitrate).
4. Stand 2–3 minutes.
5. Dip into uncured latex.
6. Stand 2–3 minutes.
7. Leach with cold tap water for 15 minutes . . . stand 2 minutes.
8. Produce ring roll.
9. Dry in oven 6 minutes.
10. Dip into 1.5% solution gentian violet in distilled water. (May substitute other biocides or chemicals in various solutions).
11. Dry in oven.
12. Stand 5 minutes.
3. Dip in 20% calcium nitrate coagulant.
4. Dip into uncured latex.
15. Stand 8 minutes.
16. Dry in oven for 30 minutes to cure by heating the membrane to dry them to their final form.
17. Powder and strip the doublet membrane from the former.

Figure 2:
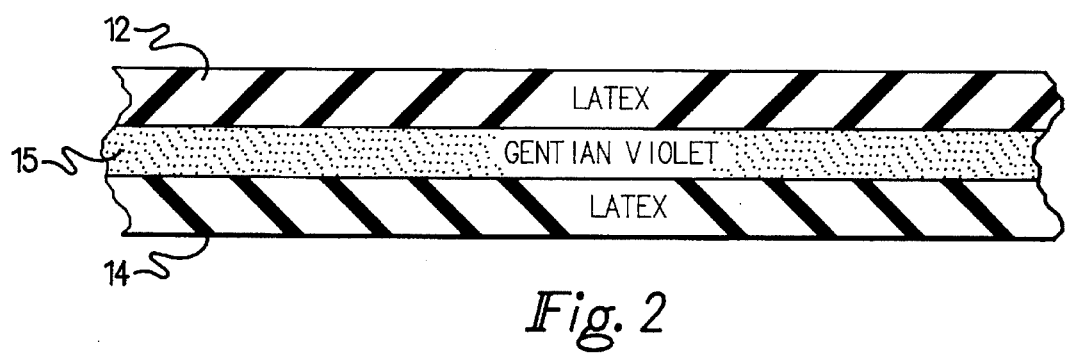
FIG. 2 is a cross-sectional view illustrating the double glove of FIG. 1 including a biocide disposed in an intermediate reservoir formed between inner and outer layers of the glove.

This method produces a glove within a glove or a condom within a condom joined at the cuff or top. FIG. 1 illustrates an example double glove 10 produced according to the invention which includes a discrete separated outer layer 12 and an inner layer 14 joined in the cuff region at a ring roll 16. As can be readily appreciated, the inventive double glove 10 has substantial advantages in ease of donning compared to separate single layer gloves. The space between the two membranes can be constructed with an additional step or steps of incorporating different substances including but not limited to gels, biocides, chemicals, silicones, neutralizing chemicals, buffering chemicals, spermicides, lubricants, and tactile enhancers. For example, as shown in FIG. 2, the reservoir 15 formed between the inner 14 and outer 12 layers of the glove may be filled with a biocide such as gentian violet.

It should be appreciated that this double membrane configuration can also be made by the above method with a biocide component by dipping in biocide before dipping in the coagulant, or by mixing the biocide or chemical with the coagulant.

The salient steps in the above method comprise:
(a) depositing onto a former a first latex layer;
(b) treating the first layer with a material effective as a coagulant for latex;
(c) depositing over the first layer on the former a second latex layer, with the coagulant effective to substantially prevent fusing of the first and second layers; and
(d) setting or curing the first and second layers.

It is particularly preferred that the coagulant is not applied to a circumferentially extending top or cuff region of the first layer such that the first and second layers will fuse in that region to form a reservoir. Prior to application of coagulant to the first layer, a substance may be deposited over the first layer on the former, with the substance selected from the group consisting of biocides, indicators, spermicides, antiseptics, gels, hydrogels, pituitous substances, cleansing agents, surfactants, detergents, abrasives, coating agents, wiping agents, fibers, tactile enhancing objects, and sheet forming agents, such that the substance is substantially contained between the first latex layer and the second latex layer.

A method of forming a polymeric multi-layer membrane according to the present invention includes the steps of:
(a) depositing onto a former a material selected from the group consisting of liquid polymers and polymers dissolved in a solvent to form a first layer;
(b) treating the first layer with a surfactant;
(c) depositing over the first layer on the former a material selected from the group consisting of liquid polymers and polymers dissolved in a solvent to form a second layer, wherein the surfactant is effective to substantially prevent fusing of the first and second layers; and
(d) setting or curing the first and second layers.

As in the method of making latex membranes, a variety of substances may be provided in an intermediate layer or reservoir between the first and second layers. Example surfactants include ionic surfactants capable of emulsifying or destabilizing polymers in a known manner.

Incorporation Of Biocide Into Polyurethane Films

Glow discharge treatment techniques can be used to enhance the pick-up and retention properties of certain polymer families.

Biocides may be more effectively picked up and retained by certain polymer films. The film may be selected from the family of glow discharge treated polymers, such as polyethylene, tetrafluoroethylene glow discharge treated PE(TFE/PE), polyethyleneterephthalate) (PET), TFE/PET, polytetrafluoroethylene (PTFE), ethylene glow discharge treated PET (E/PET) and hexamethyldisiloxane glow discharge treated PET (HMDS/PET), or any of the other polymers treated by the glow discharge process. The biocides may be directly applied to the glow discharge treated films. The resulting films may be somewhat stiffer but very strong and therefore thinner films will be satisfactory for many applications.

Alternately, the biocides may be fed, as a gas, into a chamber and directly deposited by creating the glow discharge or RF discharge to facilitate the deposition.

Additionally, the biocides may be introduced on, and/or into the polymer during the fabrication of the film in such a way as to be available to provide disinfectant properties. This can be accomplished by conventional dipping or mixing, with additional layers deposited by dipping, casting, spray coating, vacuum depositing, passing through fluidized beds, centrifugal spinning, etc. Outer coats can be formed by similar techniques to contain the biocide and minimize leaching where desirable.

Coatings within the scope of the present invention include spermicides such as Nonoxinol-9 and one or more organopolysiloxane compounds which may be applied to latex membranes as disclosed in U.S. Pat. No. 5,304,375, the entire disclosure of which is hereby incorporated by reference herein. Rubber membranes may be provided with a transparent coating of an aqueous composition containing a preformed latex binder, an emulsifying agent, an inorganic fluoro-containing compound, and a thickening agent as described in U.S. Pat. No. 5,182,142, the entire disclosure of which is hereby incorporated by reference herein. A cellulosic coating material including synthetic latex formed by emulsification of cellulosic polymers stabilized by surfactants and containing a water-soluble pore forming agent and a plasticizer may also be employed, as described in U.S. Pat. No. 5,126,146, the entire disclosure of which is hereby incorporated by reference herein.

Incorporation Of Biocide Into Porous And Non-Porous Polyurethane Films

This can be done in the four ways described below. All except the last require the biocide to have a low vapor pressure at room temperature (less than −0.013 bar). In all cases the solvents that come in contact with the biocide must not react with or chemically alter the biocide in such a way as to irreversibly destroy their anti-bacterial and anti-viral activity.

(1) Physical entrapment of the biocide in the pores of a porous film.

A. Introduction of the biocide during fabrication of the film

Such films can be fabricated using (1) a fully polymerized polyurethane dissolved in a suitable solvent, or (2) using a polyurethane prepolymer of molecular weight 1000 to 3000 dissolved in a solvent and subsequently vulcanized or cured with a crosslinking or curing agent added to the solution. In both cases, the solvents must be solvents for both the biocide and the polyurethane.

The solvents for this purpose will depend on the type of polyurethane: polyether, polyester or polyester-polyamide, and on the type of biocide. Some candidates are listed in the table below.

TABLE I

Candidate Solvents and their Solubility Parameters.

| Solvent | Solubility Parameter $(cals/cc)^{1/2}$ | Hydrogen Bonding |
|---|---|---|
| Dimethyl formamide (DMF) | 12.1 | medium |
| Dimethyl acetamide (DMF) | 10.8 | medium |
| Tetrahydrofuran (THF) | 9.1 | medium |
| Dimethyl sulfoxide (DMS) | 12 | medium |
| Dioxane 1,4 | 10 | medium |
| Phenol | | strong |
| m-Cresol | 10.2 | strong |
| Formic acid | 12.1 | strong |

TABLE I-continued

Candidate Solvents and their Solubility Parameters.

| Solvent | Solubility Parameter (cals/cc)$^{1/2}$ | Hydrogen Bonding |
| --- | --- | --- |
| Sulfuric acid | | strong |
| Methyl ethyl ketone | 9.3 | medium |
| Diethyl ketone | 8.8 | medium |
| Ethylene glycol monoethyl ether | 10.5 | medium |
| Ethylene glycol monomethyl ether | 11.4 | medium |

The use of water soluble polymers is also contemplated within the scope of the instant invention.

Mixtures of these solvents with each other and with non-solvents having solubility parameters in the range: 8 to 24 (cals/cc)$^{1/2}$ and medium or strong hydrogen bonding are also candidates.

The biocide is first dissolved in such a solvent or solvent mixture, to form a nearly saturated solution, and is then mixed with a solution of the polyurethane or urethane prepolymer in the same or similar solvent. In the case of solutions containing the polyurethane prepolymer, the curing agent (typically amines or alcohols with functionality of 2 or more) is added to the polymer plus biocide solution just prior to casting the films. Films of the resulting mixture are then cast using the methods described in the Gilding patents: U.S. Pat. Nos. 4,813,966 and 4,704,130, the entire disclosures of which are hereby incorporated by reference herein, with the following modifications.

On immersion of the cast film in the precipitation bath, and subsequently in the solvent extraction bath, there will be a tendency for the biocide to be leached out of the rubber and into the bath solution. This leaching can be reduced in two ways (1) saturate the precipitation or extraction bath with the biocide, or (2) use liquids of low polarity (having solubility parameters less than −9 (cals/cc)$^{1/2}$ and weak hydrogen bonding) in the precipitation and extraction baths. Since most biocides are strongly polar, they will tend to remain in the medium to strongly polar environment of the polyurethane rather than be extracted into the bath.

On subsequent drying and annealing, the remaining solvent is removed leaving the biocide physically trapped in the pores of the film.

B. Introduction of the biocide subsequent to the fabrication of the film.

A porous polyurethane film can be swelled with a solvent or solvent mixture from Table I, or with a mixture of such solvents with non-solvents, saturated with a biocide. In the case of a linear polyurethane, the proportion of non-solvent must be adjusted so that the solvent mixture swells the soft segments (polyether segments) of the urethane chain, but does not dissolve the polymer. During the swelling, the solvent/swelling agent carries the biocide through the polymer structure and into the pores.

After removal of the film from the biocide solution, the film is dried and annealed, which removes the swelling agent and leaves the biocide trapped in the pores as well as in the polymer matrix.

(2) Adsorption of the biocide on internal pore surfaces. This method is applicable to porous films.

The same procedures as in 1A and 1B are followed except that the extraction of the solvent or swelling agent from the rubber is accomplished mostly by immersion of the film in a non-solvent bath of low polarity (solubility parameter less than 9(cal/cc)$^{1/2}$ and weak hydrogen bonding). In this case, the non-solvent bath is not saturated with the biocide, as a consequence there will be a strong tendency for the biocide to adsorb to the polar polyurethane pore surfaces (as well as being trapped within the rubber matrix). The non-adsorbed biocide molecules in the pores will be leached out into the non-solvent leaving the adsorbed biocide on the pore surfaces. Any solvent or on solvent remaining in the films can be removed by drying and annealing.

(3) Precipitation of the biocide within the rubber matrix. This method is applicable to non-porous urethane films.

The same procedures as in 1A and 1B are used except that the methods for producing the pores, described in the Gilding patents are not applied. Instead, the films are simply cast from solution using the common film forming procedures: dip-coating, spraying, spinning, etc. In the case of prefabricated films the diffusion of the swelling agent plus biocide can be enhanced by stretching the rubber film biaxially.

Extraction of the solvent/swelling agent is accomplished by drying and annealing. A non-solvent bath saturated with biocide can also be used as in (1) but drying is preferred. As the concentration of the solvent/swelling agent in the rubber decreases, the biocide will precipitate out forming phase-separated regions within the rubber matrix.

(4) Chemical bonding of the biocide to functional groups on the polyurethane chains. This method is applicable to both porous and nonporous films.

Polyurethanes possess the advantage that the urethane and urea linkages in the chains are relatively reactive. Furthermore, the rubber can easily be formulated to have excess amine, —OH or isocyanate groups at chain ends or branch points, simply by deviating slightly from the stoichiometric proportions of 1:1 isocyanate: amine groups or isocyanate: —OH groups.

The biocide molecules can then be chemically bonded to such groups. It is important that such bonding be accomplished in such a way that the biocidal activity of these molecules is not compromised.

Such binding reactions can be carried out (1) prior to fabrication of the film, while the polyurethane or urethane prepolymer are in solution (subsequent to the addition of the crosslinking or curing agent), or (2) after fabrication of the film.

In the first case, the biocide binding reaction would take place with the polyurethane in solution. In the second case, the biocide binding reaction would take place in the swelled network of the rubber. In both cases, the solvent or swelling agent must remain inert during the binding reaction.

After reaction, the solvent or swelling agent is removed as described in sections (1) or (3). Even though the biocide is chemically bound to the polyurethane chains, it will still phase separate in the rubber matrix, but on a much finer scale than with the method described in section (3).

(5) Sealing of film surfaces.

For all the above methods, application of a final coating to seal the surfaces of the film to prevent leaching of the biocide during use or storage is highly desirable. Such a coating can be applied by a final dip in a polyurethane solution of low viscosity (low % solids), or by plasma or vapor deposition of a thin elastic polymer film.

ADMIXING OF GENTIAN VIOLET WITH LATEX

According to one aspect of the invention, gentian violet is admixed with liquid latex prior to membrane formation by dipping or spraying techniques. A wide variety of different concentrations may be used, but a 1.5% by weight solution of gentian violet is preferred. Applicant has found, that in addition to biocidal properties, the addition of gentian violet by admixing yields two unexpected results. The gentian violet appears to bind protein molecules in the latex, which yields two important benefits. First, this produces an anti-aging or anti-oxidizing effect which extends shelf life and increases tear resistance. Second, it appears to minimize allergic reactions in latex-allergic users.

MICROFIBER REINFORCEMENT

The present invention also contemplates membrane reinforcement by the addition of microfibers during the production process. Microfibers such as aramids, Kevlar, fiber glass, natural fibers, nylon, and graphite may be directly admixed with latex or polymer membrane materials either prior to, during, or after application. Such fiber reinforcement may be employed in connection with a single layer membrane, or in one or more layers of a multi-layer membrane. Fiber reinforcement may also be effected by adding one or more preformed sheet layers in a multi-layer membrane.

LIST OF BIOCIDES THAT APPLICANTS BELIEVE
ARE SUITABLE FOR USE IN CONNECTION
WITH THE DISCLOSED INVENTION

Taken From A Book Entitled CTFA Cosmetic
Ingredient Dictionary, 3rd edition, 1982, Published
by The Cosmetic, Toiletry and Fragrance
Association, Inc., Washington, D.C.

HC BLUE NO. 1
   $N^4$, $N^4$-Bls (2-Hydroxyethyl)-$N^1$-Methyl-2-Nitro-p-Phenylendlamine
HC BLUE NO. 2
   $N^1$, $N^4$, $N^4$-(2-Hydroxyethyl)-2-Nitro-p-Phenylenediamine
HC BLUE NO. 3
   Cibalan Blue FBL
HC BLUE NO. 4
HC BLUE NO. 5
HC BROWN NO. 1
   Capracyl Brown 2R
HC ORANGE NO. 1
   2-Nitro-4-Hydroxydiphenylamine
HC RED NO. 1
   4-Amino-2-Nitrodiphenylamine
HC RED NO. 3
   $N^1$-(2-Hydroxyethyl)-2-Nitro-p-Phenylenediamine
HC RED NO. 6
HC YELLOW NO. 2
   N-(2-Hydroxyethyl)-2-Nitroaniline
HC YELLOW NO. 3
   $N^1$-Tris (Hydroxymethyl)-Methyl-4-Nitro-o-Phenylenediamine
HC YELLOW NO. 5
   $N^1$-(2-Hydroxyethyl)-4-Nitro-o-Phenylenediamine
NONOXYNOL-2
   Polyoxyethylene (2) Nonyl Phenyl Ether
NONOXYNOL-4, -8
NONOXYNOL-9 IODINE
NONOXYNOL-12 IODINE
PIGMENT RED 57
PIGMENT RED 57:1
PIGMENT RED 63:1
PIGMENT RED 64:1
PIGMENT RED 112
PIGMENT VIOLET 19
PIGMENT YELLOW 1
PIGMENT YELLOW 3
PIGMENT YELLOW 12
PIGMENT YELLOW 13
PIGMENT YELLOW 73
QUINOLINE
QUINOLINE SALTS
TERPENES
TERPINEOL
VAT DYES
XANTHENE
ACID BLACK 58
   Irgalan Grey B1
ACID BLACK 107
   Lanamid Black B1.
ACID BLACK 131
   Nigrosine
ACID BLUE 9 AMMONIUM SALT
ACID BLUE 62
ACID BROWN 46
ACID BROWN 48
ACID DYES
ACID FUCHSIN
ACID GREEN 25
ACID ORANGE 7
ACID ORANGE 24
ACID RED 33
ACID RED 35
ACID RED 51
ACID RED 52
ACID RED 87
ACID RED 92
ACID RED 95
ACID VIOLET 43
ACID YELLOW 1
ACID YELLOW 3
ACID YELLOW 23
ACID YELLOW 73
ACID YELLOW 73 SODIUM SALT
D & C BLUE NO. 1 ALUMINUM LAKE
   Brilliant Blue Lake
D & C BLUE NO. 2 ALUMINUM LAKE
   Acid Blue 74, Indigetine 1A, Indigo Carmine
D & C BLUE NO. 4
   Acid Blue 9 (Ammonium Salt)
D & C BLUE NO. 6
   Indigo
D & C BROWN 1
   Resorcin Brown, Capracyl Brown
D & C GREEN NO. 3
   Aluminum Lake. Food Green 3
D & C GREEN NO. 5
   Acid Green 25
D & C GREEN NO. 6
   Solvent Green 3
D & C GREEN NO. 8
   Solvent Green 7
D & C ORANGE NO. 4
   Acid Orange 7
D & C ORANGE NO. 5

Acid Orange 11. Solvent Red 72. Dibromofluorescein
D & C ORANGE NO. 5. ALUMINUM LAKE
 Dawn Orange. Manchu Orange.
D & C ORANGE NO. 5 ZIRCONIUM LAKE
 Petite Orange. Dawn Orange. Acid Red 26. Ponceau R.
D & C ORANGE NO. 10
 Solvent 73. Dilodofluorescein.
D & C ORANGE NO. 10 ALUMINUM LAKE
 Solvent Red 73. Erythrosine G.
D & C ORANGE NO. 11
D & C ORANGE NO. 17
D & C ORANGE NO. 17 LAKE
D & C RED NO. 2 ALUMINUM LAKE
D & C RED NO. 3 ALUMINUM LAKE
D & C RED NO. 4 ALUMINUM LAKE
D & C RED NO. 6
 Lithol Rubin B
D & C RED NO. 6 ALUMINUM LAKE
D & C RED NO. 6 BARIUM LAKE
D & C RED NO. 7 CALCIUM LAKE
D & C RED NO. 7 ZIRCONIUM LAKE
D & C RED NO. 8
D & C RED NO. 8 BARIUM LAKE
D & C RED NO. 8 SODIUM LAKE
D & C RED NO. 9
D & C RED NO. 9 BARIUM LAKE
D & C RED NO. 9 ZIRCONIUM STRONTHIUM LAKE
D & C RED NO. 10
D & C RED NO. 17
D & C RED NO. 19
 Rhodamine B. Magenta
D & C RED NO. 19 BARIUM LAKE
 Rhodamine B. Magenta
D & C RED NO. 19 ZIRCONIUM LAKE
D & C RED NO. 21
D & C RED NO. 21 ALUMINUM LAKE
D & C RED NO. 21 ZIRCONIUM LAKE
D & C RED NO. 22
 Eosine YS
D & C RED NO. 27
D & C RED NO. 27 ALUMINUM LAKE
 Terabromo Terachloro Fluorescein Lake
D & C RED NO. 27 BARIUM LAKE
D & C RED NO. 27 ZIRCONIUM LAKE
D & C RED NO. 28
 Phloxine B
D & C RED NO. 30
D & C RED NO. 30 ALUMINUM LAKE
D & C RED NO. 30 CALCIUM LAKE
D & C RED NO. 31
D & C RED NO. 31 CALCIUM LAKE
D & C RED NO. 33
D & C RED NO. 34
D & C RED NO. 34 CALCIUM LAKE
D & C RED NO. 36
D & C RED NO. 36 BARIUM LAKE
D & C RED NO. 36 LAKE
 Chlorinated Para Lake. Tange Orange
D & C RED NO. 36 ZIRCONIUM LAKE
D & C RED NO. 37
 Rhodamine B-Stearate
D & C RED NO. 37 CALCIUM LAKE
 Rhodamine B. Stearate Solvent
D & C RED NO. 39
D & C RED NO. 40
D & C YELLOW NO. 5 ALUMINUM LAKE
D & C YELLOW NO. 5 ZIRCONIUM LAKE
D & C YELLOW NO. 6 ALUMINUM LAKE
D & C YELLOW NO. 7
D & C YELLOW NO. 8
 Uranine, Sodium Fluorescein, Naphthol Yellow S
D & C YELLOW NO. 10
D & C YELLOW NO. 10 ALUMINUM LAKE
D & C YELLOW NO. 11
EXT. D & C VIOLET NO. 2
EXT. D & C YELLOW NO. 7
EXT. D & C YELLOW NO. 7 ALUMINUM LAKE
FD & C RED NO. 20
FD & C RED NO. 22
FD & C RED NO. 40
FD & C YELLOW NO. 5
FD & C YELLOW NO. 5 ALUMINUM LAKE
FD & C YELLOW NO. 6
FD & C YELLOW NO. 6 ALUMINUM LAKE
SOLVENT RED 48
SOLVENT RED 49:1
SOLVENT RED 72
SOLVENT RED 73
SOLVENT VIOLET 13
SOLVENT YELLOW 13
TARTRAZINE Taken From "FEDERAL REGISTER", Vol. 43, No. 4—Friday, Jan. 26, 1978

Antimicrobial Soaps:
Cloflucarban
Para-chloro-mein-xylenof
Povidone-iodine complex
1.5 percent phenol or less aqueous/alcoholic
Triclocarbon
 Triclosan
Health-care Peronnel Handwash:
Benzalkonium chloride
Benzethonium chloride
Cofluearban
Hexylesorinal
Iodine complexed with phophate eater of alkyaryloxy polyethylene glycol
Methyl-benzethonium chloride
Nonyl phenoxypoly (ethyleneoxy) ethanol-iodine
Para-chloro-meta-xylenol
Povidene-iodine complex
1.5 percent phenol or less aqueous/alcoholic
Poloxamer-iodine complex
Tricloearban
Undecoylium chloride-iodine complex
 Patient preoperative skin preparation
Bonzalkonium chloride
Benzethonium chloride
Hexylresorcinol
Iodine complexed with phosphate ester of alkylaryloxy polyethylene glycol
Methylbenxethonium chloride
Nonyl phenoxypoly (ethyleneoxy) ethanoilodine
Para-thloro-meta-xylenol
1.5 percent phenol or less aqueous/alcoholic
Poloxamer-iodine complex
Povidene-iodine complex
Undecoylium chloride-iodine complex
 Skin antiseptic Benzalkonium chloride
Benzathonium chloride
Hexylresorcinoi
Iodine complexed with phosphate ester of alkylaryloxy polyethylene glycol
Iodine tincture
Methyl-bonzethonium chloride
Nonyl phenoxypoly (ethylencoxy) ethanoliodine
Para-chloro-meta-xylenol
1.5 percent phenol or less aqueous/alcoholic
Poloxamer-iodine complex
Povidene-iodine complex
Triclosan
Triple Dye
Undecoylium chloride-iodine complex
 Skin wound cleanser
Cloflutarban
Iodine complexed with phosphate ester of alkylaryloxy polyethylene glycol
Iodine tincture
Nonyl phenoxypoly (ethyleneoxy) ethanoliodine
Para-chloro-meta-xylenol
1.5 percent phenol or less aqueous/alcoholic
Poloxamer-iodine complex
Povidene-iodine complex
Tricloearban
Triclosan
Undecoylium chloride-iodine complex
 Skin wound protectant
Benzalkonium chloride
Benzathonium chloride
Hexylresorcinoi
Iodine complexed with phosphate ester of alkylaryloxy polyethylene glycol
Iodine tincture
Methyl-bonzethonium chloride
Nonyl phenoxypoly (ethylencoxy) ethanoliodine
Para-chloro-meta-xylenol

We claim:

1. A method of making a multi-layer membrane including at least two discrete separated layers, comprising the steps of:
    (a) depositing onto a former a first latex layer;
    (b) treating said first layer with a material effective as a coagulant for latex;
    (c) depositing over said first layer on said former a second latex layer, said coagulant effective to substantially prevent fusing of said first and second layers; and
    (d) setting or curing said first and second layers.

2. The method of claim 1, further comprising the step of treating said first latex layer with a biocide prior to step (b).

3. The method of claim 2, wherein said biocide comprises gentian violet.

4. The method of claim 2, wherein said biocide comprises Nonoxynol 9.

5. The method of claim 2, wherein said biocide comprises chlorhexidene.

6. The method of claim 2, wherein said coagulant deposited in step (c) does not contact a circumferentially extending zone on said first layer such that said first and second layers fuse together in said zone.

7. The method of claim 6, wherein said membrane comprises a glove.

8. The method of claim 6, wherein said membrane comprises a condom.

9. The method of claim 1, wherein said membrane comprises a glove.

10. The method of claim 1, wherein said membrane comprises a condom.

11. The method of claim 1, further comprising the step of depositing a substance over said first layer on said former prior to step (c), wherein said substance is selected from the group consisting of sealants, biocides, indicators, spermicides, antiseptics, gels, hydrogels, pituitous substances, cleansing agents, surfactants, detergents, abrasives, coating agents, wiping agents, fibers, tactile enhancing objects, needle treating materials, tactile enhancing liquids, tactile enhancing gels, lubricants, and sheet forming agents, such that said substance is substantially contained between said first latex layer and said second latex layer.

12. The method of claim 1, further comprising the step of depositing at least one additional layer over said second layer.

13. A multiple layer latex surgical or examination glove including at least two discrete separated latex layers fused in the absence of any adhesive or mechanical fasteners only in a cuff region of said glove.

14. The glove of claim 13, further comprising a substance disposed between said two discrete layers, said substance selected from the group consisting of sealants, biocides, indicators, spermicides, antiseptics, gels, hydrogels, pituitous substances, cleansing agents, surfactants, detergents, abrasives, coating agents, wiping agents, fibers, tactile enhancing objects, needle treating materials, tactile enhancing liquids, tactile enhancing gels, lubricants, and sheet forming agents, such that said substance is substantially contained between said first latex layer and said second latex layer.

15. A multiple layer latex condom including at least two discrete separated latex layers fused in the absence of any adhesive or mechanical fasteners only in an open end region of said condom.

16. The condom of claim 15, further comprising a substance disposed between said two discrete layers, said substance selected from the group consisting of sealants, biocides, indicators, spermicides, antiseptics, gels, hydrogels, pituitous substances, cleansing agents, surfactants, detergents, abrasives, coating agents, wiping agents, fibers, tactile enhancing objects, needle treating materials, tactile enhancing liquids., tactile enhancing gels, lubricants, and sheet forming agents, such that said substance is substantially contained between said first latex layer and said second latex layer.

17. A method of making a multi-layer membrane including at least two discrete layers, comprising the steps of:
    (a) depositing onto a former a material selected from the group consisting of liquid polymers and polymers dissolved in a solvent to form a first layer;
    (b) treating said first layer with a surfactant;
    (c) depositing over said first layer on said former a material selected from the group consisting of liquid polymers and polymers dissolved in a solvent to form a second layer, said surfactant effective to substantially prevent fusing of said first and second layers; and
    (d) setting or curing said first and second layers.

18. The method of claim 17, further comprising the step of treating said first layer with a biocide prior to step (b).

19. The method of claim 18, wherein said biocide comprises gentian violet.

20. The method of claim 18, wherein said biocide comprises Nonoxynol 9.

21. The method of claim 18, wherein said biocide comprises chlorhexidene.

22. The method of claim 17, wherein said surfactant deposited in step (c) does not contact a circumferentially extending zone on said first layer such that said first and second layers fuse together in said zone.

23. The method of claim 22, wherein said membrane comprises a glove.

24. The method of claim 22, wherein said membrane comprises a condom.

25. The method of claim 17, wherein said membrane comprises a glove.

26. The method of claim 17, wherein said membrane comprises a condom.

27. The method of claim 17, further comprising the step of depositing a substance over said first layer on said former prior to step (c), wherein said substance is selected from the group consisting of sealants, biocides, indicators, spermicides, antiseptics, gels, hydrogels, pituitous substances, cleansing agents, surfactants, detergents, abrasives, coating agents, wiping agents, fibers, tactile enhancing objects, needle treating materials, tactile enhancing liquids, tactile enhancing gels, lubricants, and sheet forming agents, such that said substance is substantially contained between said first and second layers.

28. The method of claim 17, further comprising the step of depositing at least one additional layer over said second layer.

29. A multiple layer polymeric surgical or examination glove including at least two discrete layers fused in the absence of any adhesive or mechanical fasteners only in a cuff region of said glove.

30. The glove of claim 29, further comprising a substance disposed between said two discrete layers, said substance selected from the group consisting of sealants, biocides, indicators, spermicides, antiseptics, gels, hydrogels, pituitous substances, cleansing agents, surfactants, detergents, abrasives, coating agents, wiping agents, fibers, tactile enhancing objects, needle treating materials, tactile enhancing liquids, tactile enhancing gels, lubricants, and sheet forming agents, such that said substance is substantially contained between said first and second layers.

31. A multiple layer polymeric condom including at least two discrete separated layers fused in the absence of any adhesive or mechanical fasteners only in an open end region of said condom.

32. The condom of claim 31, further comprising a substance disposed between said two discrete layers, said substance selected from the group consisting of sealants, biocides, indicators, spermicides, antiseptics, gels, hydrogels, pituitous substances, cleansing agents, surfactants, detergents, abrasives, coating agents, wiping agents, fibers, tactile enhancing objects, needle treating materials, tactile enhancing liquids, tactile enhancing gels, lubricants, and sheet forming agents, such that said substance is substantially contained between said first and second layers.

33. A method of making a multi-layer membrane, comprising the steps of:

depositing onto a former a material selected from the group consisting of sealants, polymeric latex, a polymer dissolved in a solvent, and liquid polymers to form a first layer;

depositing over said first layer a material selected from the group consisting of biocides, indicators, spermicides, antiseptics, gels, hydrogels, pituitous substances, cleansing agents, surfactants, detergents, abrasives, coating agents, wiping agents, fibers, tactile enhancing objects, needle treating materials, tactile enhancing liquids, tactile enhancing gels, lubricants, and sheet forming agents to form a second layer; and depositing over said second layer a material selected from the group consisting of sealants, polymeric latex, a polymer dissolved in a solvent, and liquid polymers to form a third layer, substantially preventing fusing of said first and third layers, such that said first and third layers are discrete and separated and said second layer is substantially contained between said first and third layers.

34. A multiple layer latex surgical or examination glove including a body portion having at least two discrete separated latex layers and a cuff portion having a single integral latex layer.

35. A multiple layer latex condom including a body portion having at least two discrete separated latex layers and an open end region having a single integral latex layer.

36. A multiple layer polymeric surgical or examination glove including a body portion having at least two discrete separated layers and a cuff portion having a single integral layer.

37. A multiple layer polymeric condom including a body portion having at least two discrete separated layers and an open end region having a single integral layer.

* * * * *